(12) United States Patent
Covi

(10) Patent No.: US 11,714,076 B2
(45) Date of Patent: Aug. 1, 2023

(54) METHODS AND KITS FOR DETERMINING SEDIMENT AND PORE WATER TOXICITY WITH DORMANT AND DEVELOPING ZOOPLANKTON AND OTHER SPECIES HAVING A DORMANT LIFE STAGE

(71) Applicant: University of North Carolina Wilmington, Wilmington, NC (US)

(72) Inventor: Joseph A. Covi, Wilmington, NC (US)

(73) Assignee: University of North Carolina Wilmington, Wilmington, NC (US)

( * ) Notice: Subject to any disclaimer, the term of this patent is extended or adjusted under 35 U.S.C. 154(b) by 0 days.

(21) Appl. No.: 16/390,336

(22) Filed: Apr. 22, 2019

(65) Prior Publication Data

US 2019/0250139 A1    Aug. 15, 2019

Related U.S. Application Data

(62) Division of application No. 15/171,224, filed on Jun. 2, 2016, now Pat. No. 10,267,782.

(60) Provisional application No. 62/169,832, filed on Jun. 2, 2015.

(51) Int. Cl.
*G01N 33/18* (2006.01)

(52) U.S. Cl.
CPC ................... *G01N 33/186* (2013.01)

(58) Field of Classification Search
CPC .............. G01N 33/186; G01N 1/2202; G01N 2001/2223; G01N 233/195; G01N 2405/00; G01N 2405/04; G01N 2405/08; G01N 2570/00; G01N 27/622; G01N 27/624; G01N 2800/26; G01N 30/724; G01N 33/487; G01N 33/48735; G01N 33/6848; G01N 33/6851; G01N 33/92; G01N 3/00; G01N 9/00; G01N 233/43504; G01N 33/5008; G01N 33/5085; G01N 33/74; A61P 43/00; C07K 2319/10; C07K 2319/60; C07K 2319/71; C07K 14/325; C12N 2501/602; C12N 2501/603; C12N 2501/604; C12N 2501/605; C12N 2501/606; C12N 2501/608; C12N 5/0696; C12N 15/1093; A61B 10/00; A61B 10/0041; A61B 10/0233; A61B 10/0283; A61B 17/00; A61B 17/320068; A61B 18/00; A61B 18/04; A61B 18/042; A61B 18/14; A61B 18/1445; A61B 18/1815; A61B 18/20; A61B 1/00013; A61B 1/041; A61B 1/2736; A61B 1/31; A61B 2010/0083; A61B 2017/320069; A61B 2018/00577; A61B 2018/00859; A61B 2018/00994; A61B 2218/002; A61B 2218/008; A61B 5/0066; A61B 5/0075; A61B 5/015; A61B 5/0507; A61B 5/055; A61B 5/14542; A61B 6/032; A61B 6/037; A61B 8/13; A61B 90/13; A61F 13/38; C12Q 1/025; C12Q 1/04; C12Q 1/18; C12Q 1/24; G06F 19/324; G06F 19/3481; G16B 20/00; G16H 10/40; G16H 15/00; G16H 50/20; H01J 49/0004; H01J 49/0027; H01J 49/0031; H01J 49/0036; H01J 49/025; H01J 49/0404; H01J 49/0409; H01J 49/0422; H01J 49/044; H01J 49/0445; H01J 49/0459; H01J 49/0463; H01J 49/0468; H01J 49/049; H01J 49/061; H01J 49/068; H01J 49/10; H01J 49/14; H01J 49/16; H01J 49/164; H01J 49/24; H01J 49/26; A01K 61/59; A01K 63/04; A01K 67/033; A01K 61/13; A01K 63/045; A01K 61/00; Y02A 40/81; Y02A 40/824; Y10S 435/967; Y10S 435/975; A01N 59/00; A23K 10/10; A23K 20/10; A23K 50/80; C02F 2303/04; C02F 3/327; Y02W 10/10

See application file for complete search history.

(56) References Cited

U.S. PATENT DOCUMENTS

| | | | |
|---|---|---|---|
| 5,094,944 A | 3/1992 | Hayes | |
| 5,932,436 A | 8/1999 | Dodson et al. | |
| 6,150,126 A * | 11/2000 | Dodson | A01K 63/04 |
| | | | 435/29 |
| 10,267,782 B2 * | 4/2019 | Covi | G01N 33/186 |
| 2012/0064180 A1 | 3/2012 | Bossier et al. | |

FOREIGN PATENT DOCUMENTS

WO    2007039508 A1    4/2007

OTHER PUBLICATIONS

EPA. Methods for Measuring the Toxicity and Bioaccumulation of Sediment-associated. EPA. 2000;1-192.*

(Continued)

*Primary Examiner* — Lynn Y Fan
(74) *Attorney, Agent, or Firm* — E. Eric Mills; Nicholas P. Stadnyk; Maynard Nexsen PC

(57) ABSTRACT

Methods for determining the toxicity of fresh-water and marine sediments and sediment pore water containing indigenous or introduced toxicants from each as a one-time analysis and/or for analysis over a period of time are provided. The present disclosure further provides kits assembled for the afore-mentioned determination. The methods and kits can be used for analyzing sediment and pore water samples from, among other locations, all environments where species having a dormant life stage may exist including, for example, natural zooplankton.

8 Claims, No Drawings

(56) References Cited

OTHER PUBLICATIONS

Jiang et al.; Heavy Metal Exposure Reduces Hatching Success of Acartia Pacifica Resting Eggs in the Sediment; Journal of Environmental Sciences; Sep. 20, 2006; pp. 733-737.
Lee et al.; Composition and Toxicity of Residual Bunker C Fuel Oil in Intertidal Sediments After 30 Years; Spill Science & Technology Bulletin; Feb. 12, 2003; pp 1-13.
Rajabi et al.; Artemia Salina as a Model Organism in Toxicity Assessment of Nanoparticles; Journal of Pharmaceutical Sciences; Feb. 24, 2015; pp. 1-6.
Covi et al.; Rotenone Decreases Hatching Success in Brine Shrimp Embryos by Blcoking Development: Implications for Zooplankton Egg Banks; PLoS One; Sep. 21, 2016; pp. 1-17.
Navis et al.; Timing Matters: Sensitivity of Daphnia Magna Dormant Eggs to Fenoxycarb Exposure Depends on Embryonic Developmental Stage; Aquatic Toxicology, vol. 159, Feb. 2015; pp. 176-183.

\* cited by examiner

METHODS AND KITS FOR DETERMINING SEDIMENT AND PORE WATER TOXICITY WITH DORMANT AND DEVELOPING ZOOPLANKTON AND OTHER SPECIES HAVING A DORMANT LIFE STAGE

CROSS REFERENCE TO RELATED APPLICATIONS

This application is a divisional of U.S. patent application Ser. No. 15/171,224 having a filing date of Jun. 2, 2016, which claims the benefit of U.S. Provisional Patent Application No. 62/169,832 filed Jun. 2, 2015, each of which is incorporated herein by reference in its entirety.

SUMMARY

The present invention provides methods for determining the toxicity of certain indigenous or introduced toxicants in fresh-water and marine sediments, sediment pore water and terrestrial samples from each as a one-time analysis and/or for analysis over a period of time. The present invention further provides kits assembled for the afore-mentioned determination. The methods and kits of the present invention can be used for analyzing sediment and pore water samples from all environments where natural zooplankton embryos or other species having a dormant life stage exist or could exist under anoxic or other controlled environmental conditions.

BACKGROUND

The United Stated Environmental Protection agency and United States Army Corps of Engineers have been seeking a method for determining the chronic toxicity of fresh water and marine bottom sediment and pore water extracted therefrom. Although certain methods have been available for using invertebrate species for evaluating the toxicity of sediment and pore water by introducing active or developing animals to the sediment and/or pore water, these tests are limited in duration due to the physiological needs of the active invertebrates used. Moreover, there appears to be no known method that would provide for determining the toxicity of such sediment and/or pore water to dormant invertebrates over an extended period of time.

DETAILED DESCRIPTION

Definitions

"Arthropod" has its common meaning as typically defined and used in the field of biology, particularly as further described herein.

"Carried out over a period of time", or variants thereof, means any period of time other than a single point in time.

"Dormant" or "Dormancy" has it common meaning as typically defined in the field of biology and includes, for example and without limitation, naturally occurring dormancy and induced dormancy via. Dormancy can be induced, for example and without limitation via: i) naturally occurring form of dormancy called diapause that does not need to be induced but does need to be maintained via, for example, protection from light, dehydration, temperature changes and oxygen levels to maintain the diapause form of dormancy. ii) quiescence is a form of dormancy induced by environmental conditions. Anoxia is the most common example. See the Hand and Podrabsky article cited below as a reference for diapause and quiescence comparison. iii. eutrophication appears to be one cue to induce dormancy in the freshwater jellyfish, as supported by the teachings of D E Culberson (1976) Studies of the encystment, excystment and general ecology of *Craspedacusta sowerbii*. Masters of Science thesis, University of South Alabama, Auburn, Ala. (hereinafter, collectively "naturally occurring or induced dormancy").

"Developmental deformity" means any deformation (development other than normal development) of an emerging or hatching zooplankton, including the inability of such zooplankton to emerge or hatch. As used herein, "developmental deformity" can also include mortality as an evaluative endpoint.

"Emerging" or "emerge" means protrusion or expulsion of a zooplankton embryo or, more generally, a species having a dormant life stage, or developing larva from its egg or cyst coat as an intermediate stage of development prior to hatching "Hatching" or "Hatch" means the release of a free-swimming zooplankton larva from any structure(s) that encapsulate the larvae during prior development.

"Indigenous" means the presence of a toxicant in one or more sediment, or pore water sample without the addition of such toxicant to the sediment or pore water.

"Lipophilic" has its common meaning as typically defined and used in the field of chemistry and includes, for example and without limitation, a substance or chemical having any degree or amount of lipophilicity. For further clarity, the term "lipophilic", as used herein, includes any compound or substance capable of penetrating the cuticle of an arthropod or other organism having a dormant state as further described herein.

"Osmolyte or Osmolytic Solution" has its traditional scientific meaning with the caveat that when used herein, the osmolyte or osmolytic solution does not penetrate the cuticle of a respective target species such that lysis would occur or otherwise interfere with the action of the respective organism.

"Pore water" means the water extracted and/or separated from a sediment sample.

"Reconstituted" means made by dissolving a specified amount of salts of various kinds in a specified volume of water to create a standardized solution.

"Sediment" has its common meaning that includes terrestrial, aquatic freshwater and aquatic marine environments. In addition, the term "sediment", as used herein, also includes terrestrial soil samples using the methods and kits described herein and/or toxicant-contaminated terrestrial soil that has been deposited and/or displaced to an aquatic freshwater and/or aquatic marine environment.

"Species Having a Dormant Life Stage" means, typically, zooplankton as further described herein. Further examples of species having a dormant life stage includes, for example and without limitation the following descriptions as set forth herein below:

*Craspedacusta sowerbyii* (Freshwater Jellyfish; podocyst is the dormant life stage);

*Acartia tonsa* (marine copepod). F Chen and N H Marcus (1997) Subitaneous, diapause, and delayed-hatching eggs of planktonic copepods from the northern Gulf of Mexico: morphology and hatching success. 127:587-597, which is herein incorporated by reference in its entirety. This paper teaches that 6 species of marine zooplankton from just one sampled location all produce dormant embryos (*Labidocera aestiva, Acartia tonsa, Centropages velificatus* and *Calano-*

*pia americana*), and two are capable of producing both dormant and non-dormant embryos (*Labidocera mirabilis* and *Centropages hamatus*);

*Boeckella poppei* and *Boeckella triarticulata* (freshwater/saline lake copepods) X Jiang, S Zaho, Z Xu, G Wang, J He, and M Cai (2012) Abundance and age of viable resting eggs of the calanoid copepod *Boeckella poppei* Mrazek in sediments: evidence of egg banks in two Antarctic maritime lakes. Polar Biology 35: 1525-1531, which is herein incorporated by reference in its entirety. This article teaches that *Boeckella poppei* has a dormant embryo;

K M Couch, M Downes and C W Burns (2001) Morphological differences between subitaneous and diapause eggs of *Boeckella triarticulata* (Copepoda: Calanoida). Freshwater Biology. 46:925-933, which is herein incorporated by reference in its entirety. This article teaches the difference in structure between embryos capable of dormancy and those that directly develop for one species of copepod (*B. triarticulaa*). *A. franciscana* also has two types of embryos like this;

*Diaptomus sanguineus* (freshwater lake copepod). N G Hairston and C M Kearns (2002) Temporal dispersal: ecological and evolutionary aspects of zooplankton egg banks and the role of sediment mixing. Integrative and Comparative Biology. 42:481-491, which is herein incorporated by reference in its entirety. This paper teaches about the fact that natural sediments maintain dormancy in egg banks of freshwater lakes, and that removal from that environment by sediment mixing is required to exit the dormant state. *D. sanguineous* is the primary example species used;

*Artemia monica* (hypersaline lake anostracan), L E Drinkwater and Crowe (1987) Regulation of embryonic diapause in *Artemia*—environmental and physiological signals. Journal of Experimental Zoology, 241:297-307, which is herein incorporated by reference in its entirety;

*Eunapius fragilis* (freshwater sponge gemmules) and *Artemia franciscana* (great salt lake and San Franscisco bay saltern anostracan), S C Hand and J E. Podrabsky (2000) Bioenergetics of diapause and quiescence in aquatic animals. Thermochimica Acta. 359:31-42, which is herein incorporated by reference in its entirety. This article teaches that diapause is an endogenously programmed form of dormancy while quiescence is an environmentally induced form of dormancy. The ordinarily skilled artisan can either set conditions to maintain diapause or set conditions to induce quiescence for this and other species having a dormant life stage as described herein;

*Anemia salina* (hypersaline lake anostracan; mono lake) and other *Artemia* species well known in the art; and

*Branchinecta gainii* (freshwater lake anostracan).

"Toxicant" means an anthropogenically released or produced material (including, for example, compound(s) and substance(s)) that is/are introduced to a freshwater, marine or terrestrial environment and collects or resides in the indigenous sediment that is or can be toxic to marine or fresh-water zooplankton and/or other species having a dormant life stage. As used herein, the term "toxicant" typically includes lipophilic compounds or substances, and can also include a material introduced to a freshwater, marine, terrestrial or pore water sample for the purposes of carrying out the processes described herein.

Description

One aspect of the present invention provides for a method of determining the toxicity of indigenous or introduced toxicants in sediment samples comprising: mixing a plurality of dormant embryos of at least one zooplankton species or, more generally, a species having dormant life stage with a sediment sample under anoxic conditions; hatching the at least one species having a dormant life stage; and observing the embryos, prelarvae and larvae of the at least one species having a dormant life stage for any developmental deformity and/or mortality.

Another aspect provides for the additional step of separating the species having a dormant life stage, frequently a zooplankton species, from the sediment by using a vessel in which the species having a dormant life stage and sediment are mixed (a "mixing vessel") prior to emergence and hatching testing.

An additional aspect provides for the additional steps of: mixing the sediment with a sucrose solution or other non-toxic osmolyte or osmolytic solution that in a vessel capable of being used in a centrifuge including for example and without limitation a mixing vessel; centrifuging the mixture from or in the mixing vessel; separating the embryos from the supernatant from the centrifuging by pouring the supernatant over a sieve or filter paper, leaving the embryos in the sieve or filter paper; and transferring the embryos to another vessel for observations related to, for example and without limitation, hatching, emergence, developmental deformity/deformities, mortality and other observations and/or tests described herein, including for example and without limitation the timing of such hatching, emergence and developmental events or that can be carried out by the ordinarily skilled artisan. The embryos can be optionally rinsed to wash off the sucrose or other osmolyte solution before the referenced transfer.

For primary or secondary school demonstrations or other instances when a centrifuge is not readily available, a string or monofilament line can be secured to an anoxic or other respective incubation chamber as described herein and swung at a high speed in a circular manner to segregate some of the or, more generally, at least one species having a dormant life stage, from a sediment sample. Alternatively, for example and without limitation, a salad spinner can be used to generate the necessary centrifugal force needed to segregate species having a dormant life stage from a sediment sample. Essentially, any device, commercially available or self-constructed, capable of providing sufficient centrifugal force required to carry out the processes described herein would be acceptable. This method is not intended to be used for quantitative experimentation but may be useful for demonstration purposes. It is suggested that additional zooplankton embryos, and/or embryos of at least one species having a dormant life stage, be introduced to the sediment samples to increase the likelihood of segregation of embryos from sediment. Appropriate safety measures need be taken when using this method. It is also recommended that a plastic tube be used for this segregation method.

Another aspect provides for a method of determining the toxicity of indigenous or introduced toxicants in sediment samples comprising: mixing a plurality of dormant embryos of at least one species having a dormant life stage with a sediment sample under conditions to maintain such dormancy; hatching the at least one species having a dormant life stage; and observing the embryos, prelarvae and larvae of the at least one species having a dormant life stage for any developmental deformity or, more generally, observing recovery from the dormant state and ensuring events associated with the continuation of the life cycle of the organism.

The present invention further provides for carrying out the methods described above over a period of time. In this instance, the length of the period of time is limited only by the experimental design and resources required to carry out the processes described herein. More specifically, such period of time can be from 1 to each of 24 hours in a day with each hour in a day being a whole and/or fractional number, one to each of seven days in a week with each day being a whole or fractional part of a day, from 1 to 52 weeks in a year with each week being a whole or fractional week, from 1 to 12 months in a year with each month being a whole or fractional month, from 1 to a plurality of whole or fractional years, and the like. In fact, the amount of time and frequency of sampling sediment or pore water is not limited in time or frequency of observation, depending upon the availability of sample materials and materials to carry out the methods and use of the kits as described herein.

When studies are carried out over a period of time, sediment and/or pore water toxicant(s) can be supplemented to better understand the level(s) of indigenous toxicant versus a known quantity relative to the hatching, emergence and development of the zooplankton species or, more generally, species having a dormant life stage. Accordingly, another aspect of the present invention provides a method of comparing indigenous sediment and pore water toxicity relative to known toxicants comprising: adding a known quantity of at least one known toxicant to at least one sediment or pore water sample; and comparing the hatching, emergence and development of the respective zooplankton species or, more generally, species having a dormant life stage, between the sample(s) containing indigenous toxicant versus samples containing supplemented toxicant.

Another aspect of the present invention provides a method for determining indigenous or introduced toxicants in pore water collected from sediment samples comprising: mixing a plurality of dormant embryos of at least one species having a dormant life stage with a the pore water sample under anoxic conditions or other conditions that will induce or maintain dormancy; hatching the at least one species having a dormant life stage; and observing the emerging embryos, prelarvae or larvae of the at least one species having a dormant life stage for any developmental deformity and/or mortality.

Another aspect provides for a method of determining the toxicity of indigenous or introduced toxicants in pore water samples comprising: mixing a plurality of dormant embryos of at least one species having a dormant life stage with a pore water sample under conditions to maintain such dormancy; hatching the at least one species having a dormant life stage; and observing the embryos, prelarvae and larvae of the at least one species having a dormant life stage for any developmental deformity or mortality or, more generally, observing recovery from the dormant state and ensuring events associated with the continuation of the life cycle of the organism.

An additional aspect provides for the additional steps for the pore water processes taught herein above of: separating the embryos from the pore water by pouring the pore water containing the at least one zooplankton species or, more generally, at least one species having a dormant life stage, over a sieve or filter paper leaving the embryos in the sieve or filter paper; and transferring the embryos to another vessel for observations related to, for example and without limitation, hatching, emergence, developmental deformity/ deformities, mortality and other observations and/or tests described herein or that can be carried out by the ordinarily skilled artisan. These methods can also be carried out over a period of time.

Also provided is a kit for determining indigenous or introduced toxicants in sediment samples comprising: a plurality of embryos of at least one zooplankton species or, more generally, at least one species having a dormant life stage; at least one dry water-preparation package selected from the group consisting of artificial ("reconstituted") freshwater mix and artificial seawater mix (each, individually, a "dry salt package"); at least one anoxic incubation container that can be purged; and a sterile receptacle for emergence and hatching testing of the zooplankton or, more generally, species having a dormant life stage. In another aspect, the anoxic incubation chamber can be replaced with vessels known to the ordinarily skilled artisan in which dormancy of the species having a dormant stage is maintained.

Another aspect provides for the addition of material to the above-described kit comprising: at least one selected from the group consisting of a squirt bottle, sieve or filter material, dry sucrose crystals or other non-toxic osmolyte or osmolytic solution, instructions including diagrams of developing or other species having a dormant life stage and tubes capable of being used in a centrifuge or other means by which to separate or segregate the species having a dormant life stage from sediment.

An additional aspect of the present invention provides for a kit for determining the toxicity of indigenous or introduced toxicants in sediment pore water samples comprising: a plurality of embryos of at least one zooplankton species or, more generally, at least one species having a dormant life stage; at least one dry salt package selected from the group consisting of artificial freshwater mix and artificial seawater mix; at least one anoxic incubation container that can be purged or other appropriate container in which dormancy of a species having a dormant life stage is induced or maintained; and a sterile receptacle for emergence and hatching testing of the zooplankton or, more generally, species having a dormant life stage, optionally also comprising at least one selected from the group consisting of a squirt bottle, instructions including diagrams of developing zooplankton or, more generally, species having a dormant life stage, and sieve or filter material; the squirt bottle and sieve or filter material being well recognized in the chemical and biological arts.

Sediment samples can be taken by any method. Typically, but without limitation, core or grab sample is taken to any desired depth for aquatic or terrestrial samples. The sediment sample can be incrementally segregated by depth or can be mixed to prepare a single homogeneous sediment sample. Sediment should be maintained under normoxic, hypoxic or anoxic conditions that most closely approximate conditions at the site of origin.

A variety of zooplankton embryos or, more generally, at least one species having a dormant life stage, can be used to carry out the methods of the present invention and can be included in the kits described herein. Typically, embryos of one or more such species is/are selected to match the environment from which a respective sediment sample is taken. For example, a species having a dormant life stage indigenous to fresh-water should be used when testing fresh-water sediment samples or samples to be added to a freshwater system and a species having a dormant life stage indigenous to a marine environment should be used when testing marine sediment samples or samples to be added to a marine system.

For example and without limitation, embryos of the salt-water (marine and hypersaline) species *Artemia franciscana* can be used for testing marine sediment and/or pore samples or used in the kits of the present invention. Typically this *Artemia* species is used/provided in a kit in a dechorionated and hydrated form. For each of the methods and kits of the present invention, the use of *Artemia* species that are known for high, consistent hatch rates are beneficial. One supplier of such zooplankton is the Great Salt Lake Brine Shrimp Cooperative (Ogden, Utah, USA). For the sake of clarity, a reference to zooplankton herein includes, for example and without limitation, references herein to any *Artemia* species. For species described and used in the methods and kits herein, the ordinarily skilled artisan will appreciate that varying methods are available for accomplishing dechorionation, as appropriate for each selected species.

Useful fresh-water embryonic zooplankton species include redtail fairy shrimp (also, typically, dechorionated and hydrated), available from, for example, Arizona Fairy Shrimp (http://arizonafairyshrimp.com) and Florida Aquafarms (http://florida-aqua-farms.com/). Additional zooplankton embryos that can be used in the present methods and kits include rotifers, *Daphnia* spp., *Triops* spp and other cultured zooplankton that are sensitive to lipophilic toxicants. Such zooplankton embryos are readily available from a variety of aquaculture suppliers.

Marine and/or fresh-water embryonic zooplankton species can be used for terrestrial soil samples depending upon the closest potential environment to such samples and/or of the experimental design of the researcher. It may be optimal to test both fresh-water and marine zooplankton species in terrestrial samples as one would not be limited to the indigenous environment providing a proper environment, as described herein, is created for the study of introduced zooplankton species. Additional species having a dormant life stage are additionally described hereinabove.

Depending upon the species of species having a dormant life stage used in the methods and kits of the present invention, dehydrated embryos (those not pre-hydrated) need to be hydrated for about 4 to about 24 hours, typically on ice prior to use. In some cases, embryos of certain species like *Daphnia magna* should be stored hydrated at 4° C., and only used after they are stored for at least 1 month.

With the present methods and for use with the kits described herein, the selected species having a dormant life stage embryos are mixed with the sediment and/or pore water sample(s) to be analyzed. Embryo hatch and conformity or deformity or lack of emergence or hatching and mortality, if present, can be determined directly with the sediment by transferring a sample of the sediment and/or pore water to another container, typically a sterile petri dish or a plurality of independent or inter-connected vessels, the latter typically being multi-well, sterile polystyrene culture plates. Twelve-well polystyrene culture plates work well when simultaneously testing multiple sediment or pore water samples. It may be beneficial to segregate sediment samples into a number of containers equal to the number of tests to be conducted prior to introducing the desired species having a dormant life stage embryo into such container.

Initially, dormant species having a dormant life stage, particularly zooplankton embryos, (supplied in the kit described herein) are mixed in with one or more sediment samples in a hatching medium, frequently in a treatment flask. The number of embryos used for each treatment to be analyzed depends upon whether the intent of the test is a single point-in-time test or tests to be run over a period of time and whether the tests are to be replicated for statistical analysis. Generally, 10 to 30 embryos per ml of hatching medium, or at least 100 embryos in total are used per individual, un-replicated test. The hatching medium can contain ordinary water, distilled water, deionized water and the like. Typically, a freshwater ("reconstituted") hatching medium is prepared using deionized water with an artificial water mix as prepared, for example, by Kluttgen (Kluttgen, B, Dulmer, U, Engles, M, Ratte, H. T., 1994. *ADaM, an artificial freshwater for the culture of zooplankton*. Water Res. 28, 743-746), which is herein incorporated by reference in its entirety. For some species of zooplankton, a dilute solution of artificial seawater with a salinity of 0.1 to 0.5 parts per thousand (ppt) can be used in place of an artificial freshwater mix. In this case, salinity is determined using methods well known in the art.

When required, an artificial seawater mix is prepared such that the salt content is about 20 ppt. Artificial seawater is commercially available from numerous outlets but, for example, can also be prepared via the method taught by Neumeyer, et al. (Neumeyer, C. H., Gerlach, J. L., Ruggerio, K. M., and Covi, J. A., 2015. *A novel model of early development in the brine shrimp, Artemia franciscana, and its use in assessing the effects of environmental variables on development, emergence, and hatching*. Journal of Morphology: 276, 342-360, which is herein incorporated by reference in its entirety).

To maintain exposure of introduced species having a dormant life stage, particularly zooplankton, over a period of time and to prevent the hatching of the selected species, it is best to maintain sediment and pore water under anoxic conditions or other conditions that will induce or maintain dormancy. Maintaining samples under anoxic or other appropriate conditions can be carried out by methods well known to the skilled artisan. One option is to place samples in small vials, typically glass vials, and purge the vials with an inert gas primarily, without limitation, nitrogen gas. Alternatively, glass vessels pre-fitted with a purging cap for purging with inert gas are readily available on the commercial market (see, e.g., Foxx Life Sciences, Salem, N.H.). The vessels described herein can be used as the afore-mentioned treatment flask wherein the sediment or pore water samples containing introduced species having a dormant life stage are maintained under anoxic or other such appropriate conditions for the desired length of time prior to hatching and observation.

A single point test can be conducted by removing the anoxic conditions or other conditions used to maintain dormancy species having a dormant life stage in a sediment sample, transferring an aliquot of the sediment and observing the hatching of the introduced species having a dormant life stage, particularly zooplankton, generally, under a microscope and typically under a dissecting microscope with 75× or greater maximum magnification.

For the purpose of evaluating the impact of toxicants on early development of species having a dormant life stage, particularly zooplankton, it is best to separate the introduced embryos from a respective sediment sample and observe individual embryos under a microscope. Separation of embryos from sediment can be carried out via a variety of processes. Generally, water from a treatment flask is decanted and sediment is mixed with a sucrose solution or other non-toxic osmolyte or osmolytic solution that does not penetrate the cuticle of a respective target species in a vessel capable of being centrifuged. When using a sucrose solution, the concentration of the sucrose solution is typically a concentration selected from the group consisting of at least 10% sucrose, at least 20% sucrose, at least 30% sucrose, at least 40% sucrose, at least 50% sucrose, at least 60% sucrose, at least 70% sucrose, at least 80% sucrose and at least 90% sucrose. Typically, a disposable 50 mL or 15 mL conical vial is useful. The mixture in the vial is then centrifuged until the sediment is separated from the remaining fluid. It has been found that centrifuging this mixture at about 1,000 rcf (relative centrifugal force) for about one minute is sufficient to separate the sediment from the selected species-containing supernatant.

Following centrifugation, the supernatant is poured over an appropriate filter device, typically a sieve, filter cloth or filter paper, to collect the embryos, the embryos optionally can be washed to remove any remaining sugar or other osmolyte, and the embryos are then transferred to an appropriate vessel or plurality of vessels from which observations are made via microscope. Observation in a sterile petri dish is one alternative. For multiple observations where individual or small groups of 2 to 100 embryos are examined repeatedly over a period of time, filtered embryos can be transferred into a plurality of separate or inter-connected vessels (each, a hatching vessel); the latter including, for example and without limitation, sterile, 12-well polystyrene culture plates.

For embryo hatch/deformity/mortality observations, an adequate number of embryos are added to each vessel (as determined by a respective experimental design. Generally, 100 or more embryos per experimental treatment group are an adequate number to generate reliable results relative to emerging or hatching ratios (the relative number of emerged or hatched embryos over the total number of embryos added to a respective emergence or hatching vessel) and any developmental deformities. To facilitate the development, emergence and hatching of one or more respective species having a dormant life stage, it is recommended that an appropriate aliquot of the afore-mentioned water (fresh or marine for a respective species), also referred to as a hatching medium, be added to each hatching vessel. Generally, 1 mL of such hatching medium in each well of a 12-well culture plate is sufficient to aid in the hatching of the afore-mentioned number of embryos. The number of embryos and the amount of hatching medium is determined by the experimental design and experience of the user of the methods and/or kits of the present invention.

Pore water samples are treated similarly to the above-described methods for sediment sample except there is no need to separate the introduced embryos from sediment, as none should be present in pore water samples. If sediment does exist in pore water samples, the above-described procedure can be used to separate embryos from such sediment.

Generally, pore water can be separated from sediment samples under a vacuum or other means. Appropriate embryos are introduced to each pore water sample that is then maintained under anoxic or other appropriate conditions as described hereinabove. Depending upon experimental design, hatch/deformity/mortality tests can be conducted directly in pore water as a single point test by removing the anoxic or other conditions used to induce or maintain dormancy and transferring a sample of embryo-containing pore water to one of the hatching vessels described above and the embryos observed accordingly.

Alternatively, embryos introduced to pore water, following the desired exposure time, can be filtered and processed for observation as described hereinabove.

Once embryos are transferred to a hatching vessel, typically containing a hatching medium, observation intervals can vary among species. To observe development, emergence and hatching and any embryo, prelarval or larval deformation, it is recommended, for example, to observe *Artemia franciscana* at least at two-hour intervals between eight and 20 hours after initiation of the observations/tests described herein at 22° C. Longer intervals are possible at colder temperatures as low as 15° C., and shorter intervals are possible at warmer temperatures as high as 28° C. Observation interval times may vary among species and experimental design intended endpoints.

Also provided herein are kits for carrying out the methods described herein.

One such kit for determining indigenous or introduced toxicants in sediment samples comprises: a plurality of embryos of at least one species having a dormant life stage, particularly a zooplankton species; at least one dry salt package selected from the group consisting of artificial freshwater mix and artificial seawater mix; at least one anoxic incubation container that can be purged; and a sterile receptacle for hatching the zooplankton or other species having a dormant life stage. In lieu of the anoxic chamber, another vessel appropriate for inducing and/or maintaining dormancy may be provided. This kit may further comprise at least one selected from the group consisting of a squirt bottle, sieve or filter material, dry sucrose crystals or other osmolyte, instructions including diagrams of developing zooplankton or other species having a dormant life stage and tubes capable of being used in a centrifuge or other means by which to separate or segregate the species having a dormant life stage from sediment.

The present invention also provides a kit for determining toxicity of indigenous or introduced toxicants in sediment pore water samples comprising: a plurality of embryos of at least one artificial freshwater mix and artificial seawater mix; at least one anoxic incubation container that can be purged; and a sterile receptacle for hatching the or other species having a dormant life stage. In lieu of the anoxic chamber, another vessel appropriate for inducing and/or maintaining dormancy may be provided. This kit may further comprise at least one selected from the group consisting of a squirt bottle and sieve or filter material.

Kits designed for sediment samples may also be readily used for testing pore water samples.

The following examples are intended only for the purpose of exemplification and are not intended to limit the scope or teachings of the instant application in any manner whatsoever.

EXAMPLES

Example 1: Overview of Kits.
i) Preparation—Depending upon the species, embryos are shipped dry and aerobic (all species, unless dechoriated/decapsulated) or hydrated and in a dormant state produced by anoxic or other conditions. If hydrated, the end user requires no preparation. If dehydrated, embryos may be shipped with a desiccant pack to maintain dry conditions. If dehydrated, embryos are rehydrated, typically with deionized water, for 4-24 hours on ice before use. In some cases, embryos of certain species like *Daphnia magna* are stored hydrated at 4° C., and only used after they are stored for at least 1 month.
ii) Primary Treatment—A plurality of at least one zooplankton or other species having a dormant life stage species are mixed with field-collected sediment and/or field-collected pore water under anoxic conditions. The number of zooplankton or other species having a dormant life stage embryos, or dormant equivalent, mixed with each sediment or pore water sample is as described herein.

iii) Separation:
  a) Hatching from sediment—The end user can test for larval deformation without separating embryos from the sediment or pore water samples by transferring the sediment and/or pore water to a petri dish or other container that is compatible with the working distance of a dissecting microscope.
  b) Separating from sediment—To evaluate the impact of sediment and toxicants on zooplankton early development, the embryos are separated from sediment by pouring off water from a treatment flask as described above and sediment is mixed at ratios of 10:1 to 1:1 for sediment to sucrose with an eighty percent (80%) sucrose solution in a disposable 50 mL or 15 mL conical vial. The mixture is then centrifuged at 1,000 rcf for one minute. Sediment particles are collected at the bottom of the vial and the embryos float in the supernatant that is poured over a sieve or filter paper for collection of the embryos. The embryos are rinsed with water, typically deionized water to remove any remaining sugar, and transferred to one or more culture plates under aerobic conditions for hatching and observation. For pore water samples, such samples are poured over filter paper, the zooplankton or other species having a dormant life stage are collected and transferred to one or more culture plates for observation during development, emergence and hatching.
iv) Emergence, Hatching and Developmental Observations—For zooplankton or other species having a dormant life stage separated from sediment or pore water, culture plates, for example and without limitation, 12-well polystyrene culture plates are prepared by placing 1 mL of an appropriate hatching medium (artificial "reconstituted" freshwater or artificial seawater as described herein) into each of the 12 wells. Depending upon the end user's experimental design, an appropriate number of the selected at least one or other species having a dormant life stage species is placed in each well. Typically, 10 to 30 embryos are transferred to each well. Observations of development, emergence and hatching of the zooplankton or other species having a dormant life stage are conducted according to experimental design and vary according to selected species. For example, observations are recommended at about 2-hour intervals for *Artemia franciscana*. A developmental flow diagram provided by the herein incorporated Neumeyer, et al. article is used for continuous monitoring and endpoint development, emergence and hatching values and an assessment of developmental progression and timing. Accordingly, experimental design using the methods and kits described herein permit qualitative evaluations for the effects of the above-described sediment and pore water samples with indigenous or supplemented toxicants over any desired length of time.

Example 2. Sediment and Pore Water Toxicity Evaluation Kit when Testing Directly from Sediment or Pore Water. Required and optional list items are listed below:
  Dormant zooplankton or other species having a dormant life stage (a plurality of at least one species)
  Dry Salt pack—one or both of an freshwater mix and/or a salt water mix
  One or a plurality of anoxic incubation containers or other containers for use to induce or maintain dormancy
  One or a plurality of culture plates (one or more sterile petri dishes or one or more multi-well, interconnected plates).
  Plastic transfer pipette or pipettes Example 3. Sediment and Pore Water Toxicity Evaluation Kit when Testing Embryos Separated from Sediment or Pore Water for detailed Observation. Required and optional items are listed below:
  Dormant zooplankton or other species having a dormant life stage (a plurality of at least one species)
  Dry sucrose crystals or other osmolyte
  Dry Salt pack—one or both of an freshwater mix and/or a salt water mix
  One or a plurality of anoxic incubation containers or other containers used to induce or maintain dormancy
  One or a plurality of culture plates (one or more sterile petri dishes or one or more multi-well, interconnected plates)
  One or a plurality of conical tubes for centrifugation
  One or a plurality of plastic squirt bottles
  One or a plurality of sieves, filter cloth or filter papers.
  One or a plurality of plastic pipettes
  One or a plurality of spatulas.

Example 4. Instructions for using the kits described herein comprise, for example, the teachings for using kits as set forth herein and are very broad to describe the broad range of tests that can be carried out according to the teachings contained herein or are specific for specific end-user needs such as, for example and without limitation, instructions for using the kits for sediment or pore water collected from fresh-water or marine environments.

Example 5. Items typically not, but may be, provided in Kit:
  Inert gas, gas regulator and hose for purging anoxic incubation containers
  Deionized water
  Centrifuge
  Dissecting microscope
  String, monofilament line or salad spinner
  Conductivity meter or refractometer
  Balance for determining mass.

That which is claimed:

1. A method for determining sediment toxicity caused by at least one of an indigenous and introduced toxicant in fresh water sediment, marine sediment, or terrestrial soil samples, or sediment pore water, the method comprising:
  collecting a sediment sample:
  selecting a plurality of dormant embryos of at least one species having a dormant life stage;
  mixing the plurality of dormant embryos with the sediment sample via an incubation container under conditions that induce or maintain dormancy with respect to the dormant embryos;
  separating the plurality of dormant embryos from the sediment sample thereby enabling an evaluation of emergence, hatching, development, and mortality, wherein the separating comprises mixing the sediment sample comprising the plurality of dormant embryos with an osmolytic solution in the incubation container; and
  determining a presence of a toxicant in the sediment sample based on one or more deviations from a normal lifecycle corresponding to the species, wherein the determining comprises a simultaneous evaluation of emergence, hatching, developmental deformity, mortality, altered developmental rate, and altered developmental timing with respect to hatching and emergence based on the normal lifecycle.

2. The method of claim 1, wherein the separating further comprises:
   centrifuging the mixture of the sediment sample and the osmolytic solution to generate a pellet and a supernatant, the supernatant containing the plurality of dormant embryos;
   separating the plurality of dormant embryos from the supernatant by pouring the supernatant over at least one of a sieve and filter paper; and
   transferring the embryos to a vessel for evaluating the one or more deviations from the normal lifecycle.

3. The method of claim 1, wherein the sediment sample is mixed with the osmolytic solution at a ratio of about 10:1 to about 1:1.

4. The method of claim 2, wherein a percent concentration of the osmolytic solution is selected from the group consisting of at least 10%, 20%, 30%, 40%, 50% and 60%.

5. The method of claim 1 wherein the method is carried out multiple times over a pre-determined period of time.

6. The method of claim 1, wherein the at least one species having a dormant life stage comprises a zooplankton.

7. The method of claim 6, wherein the zooplankton is an *Artemia* species.

8. The method of claim 4, wherein the osmolytic solution is a sucrose solution.

* * * * *